(12) United States Patent
Salisbury et al.

(10) Patent No.: US 8,399,700 B2
(45) Date of Patent: Mar. 19, 2013

(54) VINYL ACETATE PRODUCTION PROCESS

(75) Inventors: Brian Salisbury, Oxford, PA (US); Michael E. Fitzpatrick, League City, TX (US); Wayne Joseph Brtko, Glen Mills, PA (US); Noel C. Hallinan, Loveland, OH (US)

(73) Assignee: Lyondell Chemical Technology, L.P., Houston, TX (US)

( * ) Notice: Subject to any disclaimer, the term of this patent is extended or adjusted under 35 U.S.C. 154(b) by 165 days.

(21) Appl. No.: 13/087,785

(22) Filed: Apr. 15, 2011

(65) Prior Publication Data

US 2012/0264970 A1    Oct. 18, 2012

(51) Int. Cl.
*C07C 67/28* (2006.01)
(52) U.S. Cl. ....................................................... 560/243
(58) Field of Classification Search ........................ None
See application file for complete search history.

(56) References Cited

U.S. PATENT DOCUMENTS 6,420,595 B1 * 7/2002 Hallinan et al. .............. 560/245

FOREIGN PATENT DOCUMENTS

DE    100 30 040 C1    10/2001
WO    WO2011/043798 A1    4/2011

OTHER PUBLICATIONS

PCT International Search Report and Written Opinion Mailed Sep. 11, 2012, for PCT application No. PCT/US/2012/033621.

* cited by examiner

*Primary Examiner* — Paul A Zucker

(57) ABSTRACT

A process is disclosed for the production of vinyl acetate where a mixture of ethylene, acetic acid, and oxygen is reacted in the presence of a catalyst to produce a product mixture of vinyl acetate, ethylene, carbon dioxide, acetic acid, water, ethyl acetate, and ethylene glycol diacetate. The product mixture contains both a gaseous phase and a liquid phase, which are separated. The gas phase contains at least carbon dioxide, which is removed via gas stream. The crude vinyl acetate stream is removed via a liquid stream. The crude vinyl acetate is then further separated to isolate a stream containing at the majority of the ethylene glycol diacetate. The ethylene glycol diacetate stream is then methanolyzed in the presence of a methanolyzing catalyst, to recover methyl acetate, which can be optionally recycled as a feed stock to an acetic acid plant.

11 Claims, 5 Drawing Sheets

Hydrolysis

2:1 Moral ratio MeOH : EGDA 22.5°C. Timespan: 6.5 hours

2:1 Moral ratio MeOH : EGDA 0.0°C. Timespan: 6.5 hours

2:1 Moral ratio MeOH : EGDA 22.5°C. No PTSA Timespan: 6.5 hours

VINYL ACETATE PRODUCTION PROCESS

FIELD OF THE DISCLOSURE

The disclosure relates to the preparation of vinyl acetate. More particularly, the disclosure relates to improving the overall yield of acetic acid and vinyl acetate processes by recovering methyl acetate from a reaction waste stream that comprises ethylene glycol diacetate.

BACKGROUND OF THE DISCLOSURE

Vinyl acetate is commonly produced by the reaction of ethylene, oxygen and acetic acid in the presence of a palladium-gold catalyst. See, for example, U.S. Pat. No. 3,743,607. Palladium and gold are expensive precious metals. Therefore, many efforts have been made to increase the catalytic activity and reduce the amount of catalyst needed. For example, U.S. Pat. No. 6,022,823 teaches calcining the support impregnated with palladium and gold salts prior to reducing the metals. The catalyst shows improved activity. These prior patents are herein incorporated by reference in their entirety.

The acetoxylation of ethylene to vinyl acetate is commonly performed in a gas phase, fixed bed tubular reactor. Vinyl acetate is recovered by condensation and scrubbing, and purified by distillation. Unreacted ethylene, oxygen and acetic acid are recovered by distillation and recycled to the acetoxylation.

In addition to vinyl acetate, the acetoxylation produces a number of byproducts, including carbon dioxide, water, ethyl acetate and ethylene glycol diacetate. Carbon dioxide is primarily produced by the combustion of ethylene and vinyl acetate. Carbon dioxide is removed from the reaction product mixture by distillation and absorption with a potassium carbonate solution.

Copending U.S. patent application Ser. Nos. 12/587,580, filed on Oct. 9, 2009, and 12/653,144 filed on Mar. 8, 2010 disclose a process for the production of vinyl acetate. The processes comprise reacting ethylene, acetic acid, and oxygen in the presence of a catalyst to produce a reaction mixture comprising vinyl acetate, ethylene, carbon dioxide, acetic acid, water and ethylene glycol diacetate. The reaction mixture is separated to a gas stream comprising ethylene, oxygen, and carbon dioxide and a crude vinyl acetate stream comprising vinyl acetate, acetic acid and ethylene glycol diacetate. An ethylene glycol diacetate stream is isolated from the crude vinyl acetate stream and hydrolyzed prior to or in the waste acid stripper column of an acetic acid plant, to recover the acetate content of the stream as acetic acid.

However, the hydrolysis pathway provides a number of logistical complexities that can be improved. These include maintaining a proper flow rate to a waste acid stripper, energy intensive separation of acetic acid from water, and a less than desirable equilibrium yield.

Accordingly, a new method for recovering acetic value from the vinyl acetate production is needed.

SUMMARY OF THE DISCLOSURE

Disclosed herein is a process for the production of vinyl acetate. The process comprises reacting ethylene, acetic acid and oxygen in the presence of a catalyst to produce a reaction mixture comprising vinyl acetate, ethylene, oxygen, carbon dioxide, acetic acid, water, ethyl acetate, and ethylene glycol diacetate. The reaction mixture is separated to a gas stream comprising ethylene and carbon dioxide and a crude vinyl acetate stream comprising vinyl acetate, acetic acid, water, ethyl acetate and ethylene glycol diacetate. An ethylene glycol diacetate stream is isolated from the crude vinyl acetate stream and subjected to a reactive distillation involving methanolysis to recover methyl acetate, which is preferably recycled to an acetic acid plant as a feedstock, thereby improving the overall yield of the overall process.

BRIEF DESCRIPTION OF THE DRAWINGS

In order to describe the manner in which the above-recited and other advantages and features of the present disclosure can be obtained, a more particular description of the various embodiments briefly described above will be rendered by reference to the appended drawings. Understanding that these drawings depict only exemplary embodiments and are not therefore to be considered to be limiting of its scope, and will be described and explained with additional specificity and detail through the use of the accompanying drawings in which.

DETAILED DESCRIPTION OF THE DISCLOSURE

Figure 1:
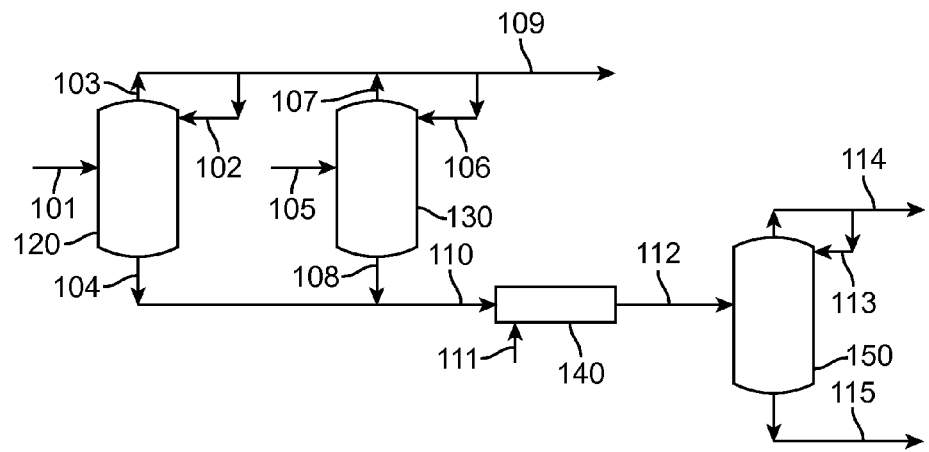
FIG. 1 is a schematic representation of an example system embodiment according to the present disclosure.

Several embodiments of the process disclosed herein includes reacting ethylene, acetic acid, and oxygen in the presence of a catalyst. The acetoxylation can be performed in a gas phase, fixed bed tubular reactor using a supported catalyst. The acetoxylation can be performed at a temperature within the range of 150 degrees Celsius to 250 degrees Celsius, or preferably within the range of 175 degrees Celsius to 200 degrees Celsius. The acetoxylation can be performed under a pressure within the range of 50 psia to 150 psia, or preferably within the range of 70 psia to 140 psia.

The amount of oxygen in the combined feed can be within the range of 5 mol % to 15 mol %, preferably within the range of 5 mol % to 12 mol %. Acetic acid can be introduced into the reactor in vapor form. The amount of acetic acid in the combined feed can be within the range of 10 mol % to 25 mol %.

The amount of ethylene in the combined feed can be within the range of 65 mol % to 80 mol %. Ethylene, oxygen and acetic acid can be mixed and the mixture can then be fed into the reactor as a gas.

Suitable catalysts include those known to the vinyl acetate industry. The catalyst can be a palladium-gold catalyst. Methods for preparing palladium-gold catalysts are known. For instance, U.S. Pat. No. 6,022,823, the teachings of which are incorporated herein by reference, teaches how to prepare a palladium-gold catalyst that has high activity and selectivity. The palladium-gold catalyst can be supported on an inorganic oxide. The inorganic oxide can be selected from the group consisting of alumina, silica, titania, and the like, and mixtures thereof.

The supported catalysts can have palladium contents from 0.1 wt % to 10 wt % and gold contents from 0.1 wt % to 3 wt %. Preferred catalysts can contain from 0.5 wt % to 1.5 wt % of palladium; and from 0.25 wt % to 0.75 wt % of gold. The weight ratio of palladium to gold can be within the range of 5:1 to 1:3, preferably within the range of 2.5:1 to 1:1.5.

The reaction mixture can be withdrawn from the reactor and separated into a gas stream and a crude vinyl acetate stream. The gas stream comprises ethylene and carbon dioxide. The crude vinyl acetate stream comprises vinyl acetate, acetic acid, water, ethyl acetate, and ethylene glycol diacetate. Carbon dioxide is separated by distillation or absorption from ethylene, which is then preferably recycled to the acetoxylation reactor. The crude vinyl acetate stream is separated by distillation into an ethylene glycol diacetate stream which comprises ethylene glycol diacetate, acetic acid and water and a vinyl acetate product stream which comprises vinyl acetate and ethyl acetate. The vinyl acetate product stream can be subjected to further purification to produce vinyl acetate with a desired purity.

The ethylene glycol diacetate stream may also comprise other components, for example, ethylidene diacetate, ethylene glycol, and polyvinyl acetate. The ethylene glycol diacetate stream preferably comprises at least 50 wt % of ethylene glycol diacetate. More preferably, the ethylene glycol diacetate stream comprises from 50 wt % to 95 wt % of ethylene glycol diacetate. Most preferably, the ethylene glycol diacetate stream comprises from 70 wt % to 80 wt % of ethylene glycol diacetate and from 20 wt % to 30 wt % acetic acid.

The ethylene glycol diacetate stream undergoes a reaction in a boiling pot reactor 140 using a methanolysis pathway, as seen in FIG. 1. FIG. 1 shows that the bottoms 104 of ARU Tower B 120 and bottoms 108 of ARU Tower C 130 are fed via line 110 into methanolysis reactor 140. Methanolysis reactor 140 is also fed with methanol via line 111. The reaction in methanolysis reactor 140 typically takes place within the range of about 60 degrees Celsius up to about 80 degrees Celsius. Furthermore, the methanolysis reactor can operate within a range having a lower limit and/or an upper limit, each expressed in degrees Celsius. The range can include or exclude the lower limit and/or the upper limit. For example, the temperature lower limit and/or upper limit can be: 50, 55, 60, 61, 62, 63, 64, 65, 66, 67, 68, 69, 70, 71, 72, 73, 74, 75, 76, 77, 78, 79, 80, 85, 90 degrees Celsius.

The reaction in the boiling pot reactor takes place in the presence of a methanolysis catalyst. Suitable methanolysis catalysts include base and acid catalysts. Examples of base catalysts include ammonia, organic amines, metal hydroxides, basic ion-exchange resins, and the like, and mixtures thereof. Examples of acid catalysts can include any strong acid, for example sulfuric acid, sulfonic acids, acidic ion-exchange resins, and the like, and mixtures thereof. The methanolysis product comprises methyl acetate and ethylene glycol that are then further separated by distillation. These products from the reaction are then fed into a distillation column 150 to separate the desired products, in particular methyl acetate.

The distillation column 150 can typically operate with a distillate stream 114 between about 50 degrees Celsius and about 70 degrees Celsius. Specifically, the distillate stream can be within the range having a lower limit and/or an upper limit, each expressed in degrees Celsius. The range can include or exclude the lower limit and/or the upper limit. For example, the temperature lower limit and/or upper limit can be: 40, 45, 50, 51, 52, 53, 54, 55, 56, 57, 58, 59, 60, 61, 62, 63, 64, 65, 66, 67, 68, 69, 70, 75, and 80 degrees Celsius. The bottoms stream of distillation column 150 can typically operate between about 140 degrees Celsius and about 160 degrees Celsius. Specifically, the bottoms stream can be within the range having a lower limit and/or an upper limit, each expressed in degrees Celsius. The range can include or exclude the lower limit and/or the upper limit. For example, the temperature lower limit and/or upper limit can be 130, 135, 140, 141, 142, 143, 144, 145, 146, 147, 148, 149, 150, 151, 152, 153, 154, 155, 156, 157, 158, 159, 160, 165, and 170 degrees Celsius.

The resultant methyl acetate is removed from the system via the distillate stream 114 and recycled to an acetic acid plant as a feedstock, the ethylene glycol is isolated as a byproduct. While a boiling pot reactor is described as facilitating the reaction, other vessels can be used, non-limiting examples include, any known continuous or batch type reactors, including fluidized bed reactors or reactive distillation. Optionally, additional amounts of water can be fed together with the ethylene glycol diacetate stream. Alternatively, additional water can be fed separately into the reaction section. The boiling pot reactor is connected to distillation column 150.

The overhead stream comprises methyl acetate and any excess methanol and it is preferably recycled to an acetic acid plant for recovery or reuse of the acetic value. The bottoms stream comprises ethylene glycol, the methanolysis catalyst, and all other heavy byproducts. The bottoms stream can be subjected to further separation or disposed of as waste.

Figure 4:
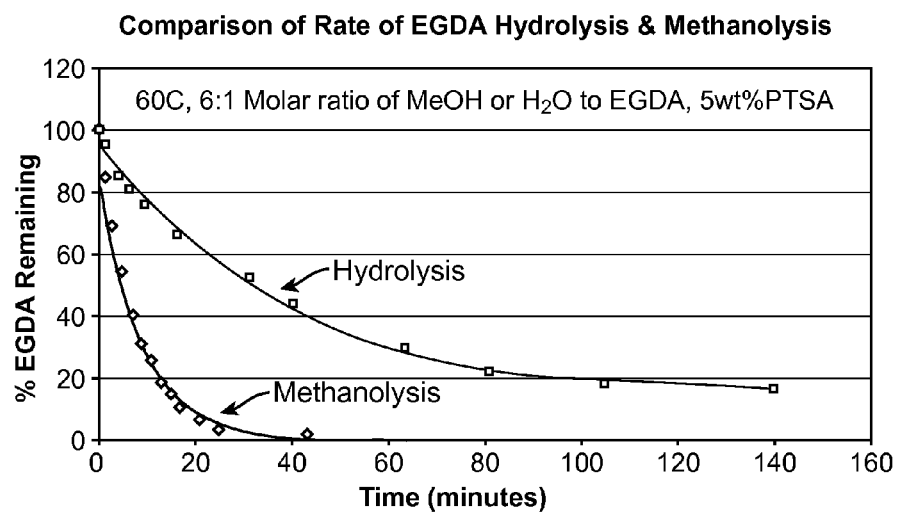
FIG. 4 is a graphic illustration of the relative reaction rates of hydrolysis versus methanolysis.

One advantage of using the herein described methanolysis pathway is that the rate of methanolysis is at least four times greater than the rate of hydrolysis, see for example, FIG. 4. Below Equation 1 represents one possible methanolysis process:

$$CH_3C(O)OCH_2CH_2O(O)CCH_3 + 2CH_3OH \rightarrow HOCH_2CH_2OH + 2CH_3COOCH_3$$

(Ethylene Glycol Diacetate)+(Methanol)→(Ethylene Glycol)+(Acetic Acid)  Equation 1

A further advantage is that the reaction produces methyl acetate from which the acetic value of ethylene glycol diacetate can be recovered. Because neither water or acetic acid are used in the reaction or produced by the reaction, the methanolysis pathway does not require the energy intensive separation of acetic acid and water. Rather, methyl acetate is produced which can be returned as feed to an acetic reactor. Finally, even though both the hydrolysis and the methanolysis pathways are in equilibrium, lying at about 80-90% to the right, if the methyl acetate is vented, the methanolysis pathway can achieve about 100% completion.

To further explain the process of the present disclosure, experiments were conducted. As described below with respect to experiments, Experiments 1 and 2 describe one embodiment of the herein described methanolysis reaction.

Figure 2:
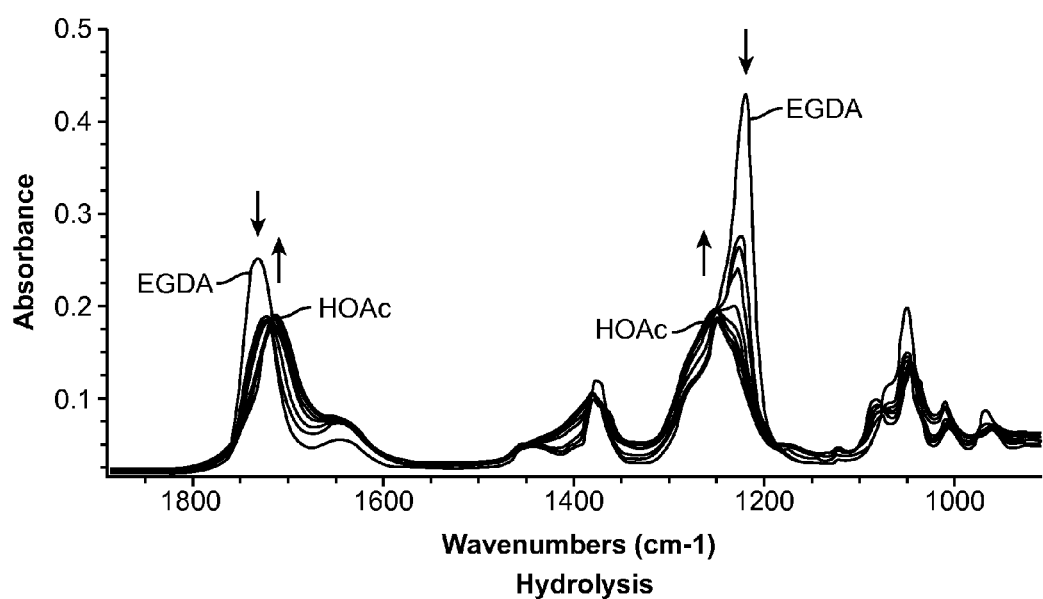
FIG. 2 is a graphic illustration of the overlaid infrared spectra obtained during the course of a reaction using a hydrolysis pathway.

Further, a hydrolysis reaction was also carried out under similar conditions to the methanolysis reaction described in Examples 1 and 2 to facilitate comparison between the two reactions. The spectra from the hydrolysis runs are included in FIG. 2, showing the production of acetic acid ("HOAc") as the ethylene glycol diacetate ("EGDA") concentrations decrease.

Figure 3:
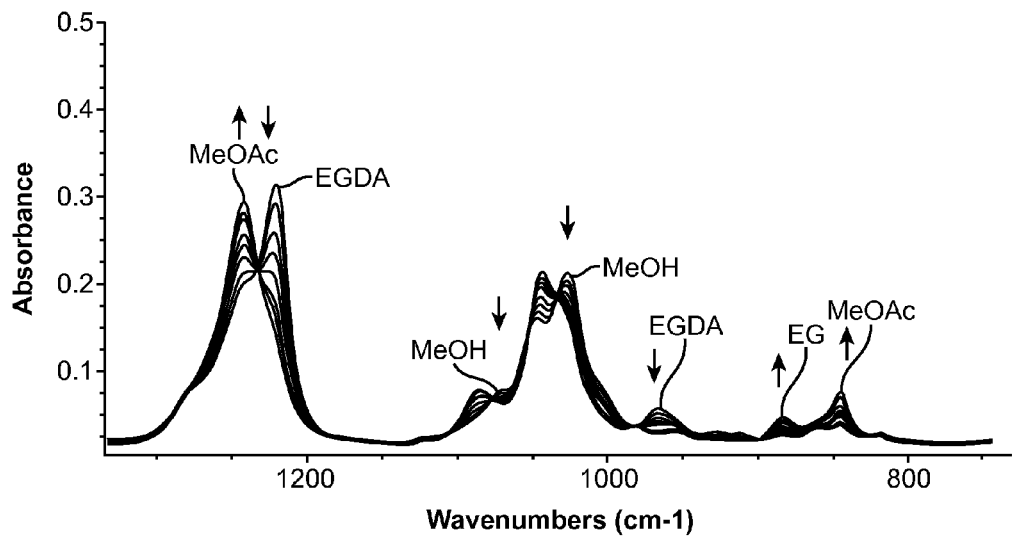
FIG. 3 is a graphic illustration of the overlaid infrared spectra obtained during the course of a reaction of 2:1 Molar ratio MeOH:EGDA at 22.5 degrees Celsius over a time span of 6.5 hours.

Based on the observations from methanolysis experiments described in Experiments 1 and 2, along with the hydrolysis reaction carried out under similar reaction conditions, several dozen multi-component calibration standards were prepared and calibration models were constructed. Those skilled in the art of infrared spectroscopy and chemometric modeling as described in U.S. Pat. No. 6,552,221 will recognize from FIG. 3 that the concentrations of the ethylene glycol diacetate, methanol, methyl acetate, and ethylene glycol can be determined from the spectra.

Based on these calibration models, the reactions can be properly monitored and the relative rates of hydrolysis and methanolysis can be determined and compared. As shown in FIG. 4, the data indicate that at 60 degrees Celsius and with 5 wt % acid catalyst, methanolysis has a half-life of about 7-8 minutes, making it about 4.5 times faster than hydrolysis. Further, products formed by methanolysis include methyl acetate, which is an easier product to separate than the products of hydrolysis, namely acetic acid and water. Therefore, the methanolysis process has rates that are substantially faster and products that are easier to isolate, than the hydrolysis pathway.

Figure 5:
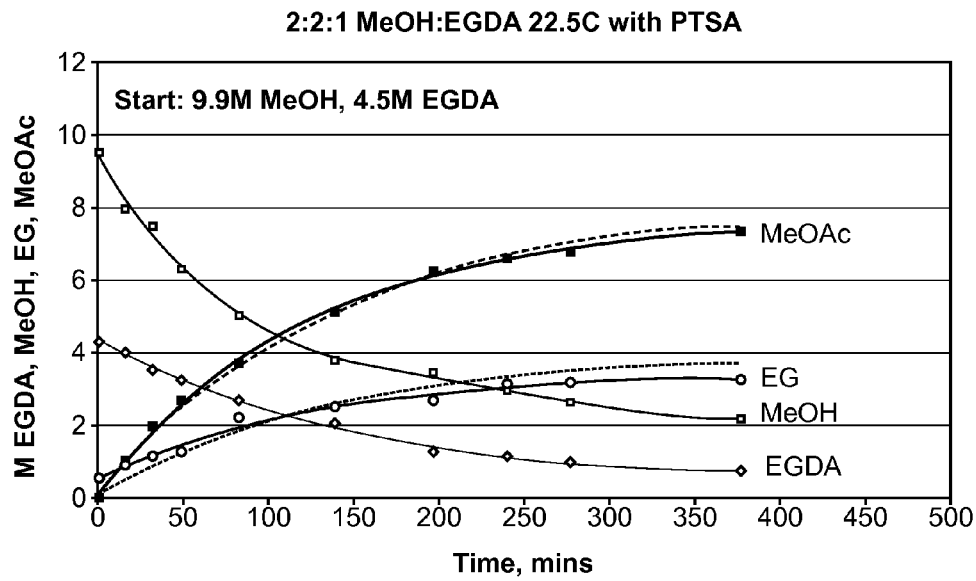
FIG. 5 is a graphic illustration of the products produced by a reaction of 2:1 Molar ratio MeOH:EGDA at 22.5 degrees Celsius in the presence of a catalyst.

The calibration models available were also used to provide a material balance during a methanolysis reaction. The material balance shows that EGDA is methanolyzed to about 100% ethylene glycol ("EG"), rather than methanolyzed at a lower rate, which leads to a mixture of the glycol and monoacetate. As shown in FIG. 5, the reaction produces glycol almost exclusively, i.e., it is about 100% methanolyzed. The molar disappearance of EGDA is matched by a corresponding molar appearance of EG and a two-fold molar appearance of MeOAc. The calibration models were applied to the spectroscopic data for a room temperature methanolysis reaction and the corresponding quantitative data are shown in FIG. 5.

In addition to the quantitative data obtained from the calibration models, FIG. 5 also contains dashed line curves for MeOAc and EG that were calculated on the assumption that the measured EGDA disappearance can be attributed solely to complete methanolysis to two moles of MeOAc and one mole of EG per mole of EGDA. Specifically, the methanolysis pathway comprises at least the following stepwise reactions:

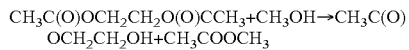

(Ethylene Glycol Diacetate)+(Methanol)→(Ethylene Glycol Monoacetate)+(Methyl Acetate)      Equation 2

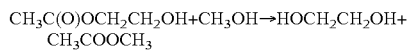

(Ethylene Glycol Monoacetate)+(Methanol)→(Ethylene Glycol)+(Methyl Acetate)      Equation 3

With regard to FIG. 5, if the ethylene glycol monoacetate formed in Equation 2 immediately reacts with another $CH_3OH$ as shown in Equation 3, it will not be observed on the infrared timescale and 2:1 molar relationship between disappearance of EGDA and appearance of MeOAc would be expected and so would a 1:1 molar relationship between disappearance of EGDA and appearance of EG. Using these assumptions, at any time point during a methanolysis where an infrared spectrum is obtained, the concentration of MeOAc should be (EGDA initial−EGDA time point)*2 where the EGDA time point concentration is determined from infrared. Based on this logic, the MeOAc time point concentration determined from infrared should match the value determined in the MeOAc concentration definition above.

Based on the close overlap between the measured and calculated values for MeOAc and EG, the methanolysis reaction described by this embodiment produces very low, if any, steady state concentrations of the monoacetate. Furthermore, this quantitative analysis shows that the reaction reaches at least 90% completion, and can reach 100% completion.

Figure 6:
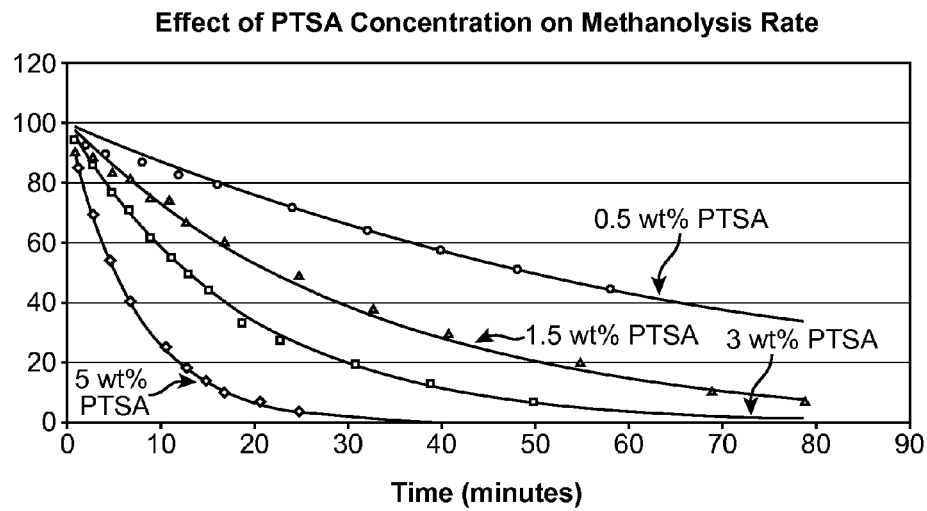
FIG. 6 is a graphic illustration of the effect of catalyst concentration on methanolysis rate.

Based on the quantitative analysis, the kinetics of the methanolysis reaction can be determined. Initially, the overall methanolysis reaction can be predicted to be $4^{th}$ order with $1^{st}$ order dependence on EGDA and the acid catalyst, and $2^{nd}$ order dependence on MeOH. As acid catalyst concentration will be relatively invariant in an industrial process, the reaction at constant acid catalyst concentration can be considered to be pseudo $3^{rd}$ order. To confirm that the reaction does have a $1^{st}$ order dependence on catalyst concentration, several reactions were carried out at 49 degrees Celsius in which a starting MeOH:EGDA molar ratio of 6:1 was maintained and in which para-toluenesulfonic acid ("PTSA") concentration was varied from 0.5 to 5.0 wt %. Reaction profiles in terms of disappearance of EGDA are shown in FIG. 6 and $1^{st}$ order dependence was confirmed.

Figure 7:
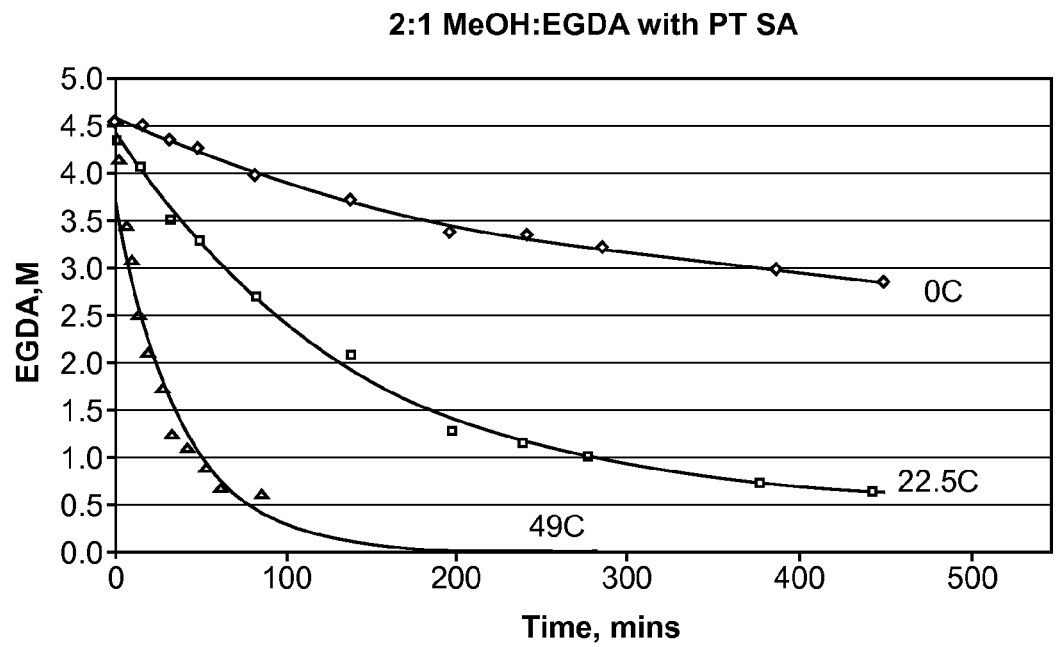
FIG. 7 is a graphic illustration of the effect of temperature on methanolysis rate.

FIG. 7 shows some reaction profiles for temperatures ranging from 0 to 49 degrees Celsius. Generally speaking, duplicate runs were carried out. Rate constants associated with runs at select temperatures are shown in Table 2.

TABLE 2

| Temp, ° C. | k, $M^{-1}s^{-1}$ |
| --- | --- |
| 19 | 2.66E−05 |
| 19 | 2.49E−05 |
| 34 | 5.67E−05 |
| 34 | 6.33E−05 |
| 49 | 1.95E−04 |

In an effort to simulate industrial conditions where temperatures in excess of 60 degrees Celsius will be used to allow MeOAc evaporation, thus driving the equilibrium to completion, several runs in the 60-65 degrees Celsius range were carried out with a water cooled condenser. It was indeed observed over the course of a high temperature run that measured MeOAc concentrations did not achieve material balance relative to disappearance of EGDA. It was found that these high temperature runs showed complete disappearance of EGDA, complete formation of ethylene glycol and about 70% of expected MeOAc concentration. These data suggest that an equilibrium position close to 100% can be expected using temperatures in excess of 60 degrees Celsius.

The following examples are merely illustrative. Those skilled in the art will recognize many variations that are within the spirit and scope of the disclosure.

EXAMPLES

The following examples were carried out to test the properties of the reaction under multiple different reaction conditions. Reaction runs were carried out using a 50 mL Schlenk flask equipped with a condenser, with 20 mLs of total solution used per run. The Schlenk flask containing the required volume of MeOH and required weight of PTSA was heated to desired temperature in a water bath. Simultaneously, the required volume of EGDA, contained in a vial, was also heated in the water bath. Once solutions had reached desired temperature, EGDA was rapidly syringed from the vial and via a one foot long needle was added to the Schlenk flask through the condenser.

Subsequently the solution was monitored on a periodic basis, the frequency of which depended on the rapidity of the reaction. Aliquots of 0.1 mL were removed by a disposable syringe equipped with a one foot long needle which could be inserted through the side arm of the Schlenk flask and into the solution and analyzed by ATR-FTIR. The lowest achievable frequency of analysis was 2 minutes.

Example 1

Figure 8:
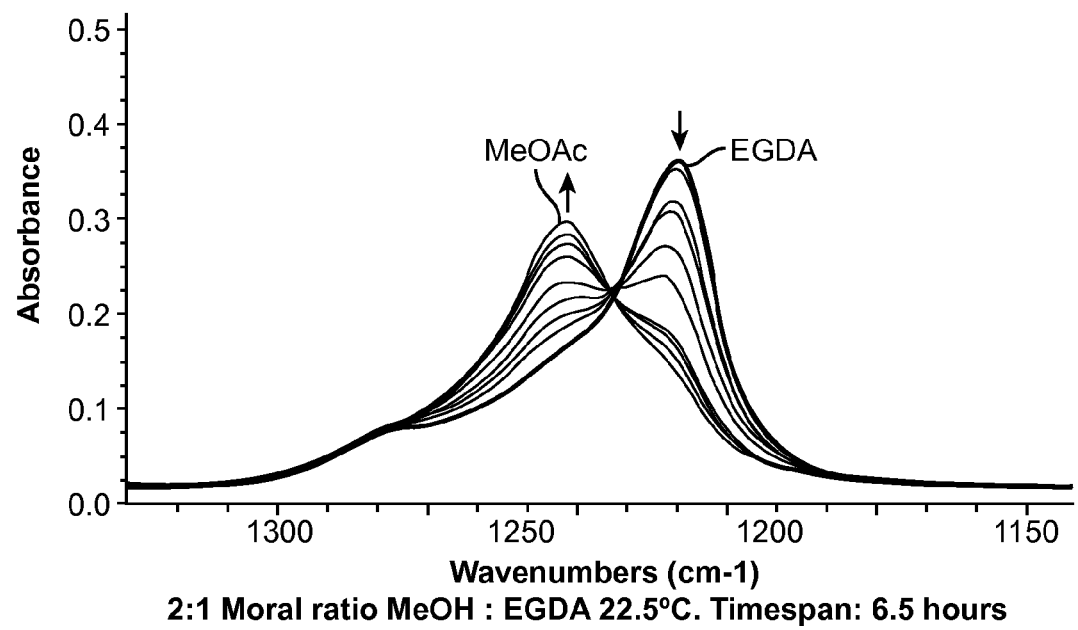
FIG. 8 is a graphic illustration of a narrower spectrum of the reaction detailed in FIG. 2.

A methanolysis run was carried out at 22.5 degrees Celsius with a solution comprising 2.2:1 molar ratio of MeOH:EGDA with 5 wt % PTSA catalyst. FIG. 8 contains overlaid spectra obtained over a period of 6.5 hours. Reactions were carried out for both methanolysis and hydrolysis and analysis by GC at run termination indicated that rates were sufficiently slow to allow monitoring by periodic FTIR analysis. In order to identify spectroscopic features and as a guide to aid in generation of the multicomponent calibration models required for data analysis, a few methanolysis runs were carried out in which the solutions were periodically monitored by removal of aliquots for FTIR analysis.

The methyl acetate peak, the left most peak labeled MeOAC, rises as the ethylene glycol diacetate peak, the right most peak labeled EGDA, falls. This indicates that the methyl acetate is formed by the disappearance of EGDA, as predicted by Equation 1. Furthermore, the reaction appears to consume most of the EGDA present at the beginning of the reaction, as indicated by the lack of absorbance at about 1220 $cm^{-1}$.

Example 2

Figure 9:
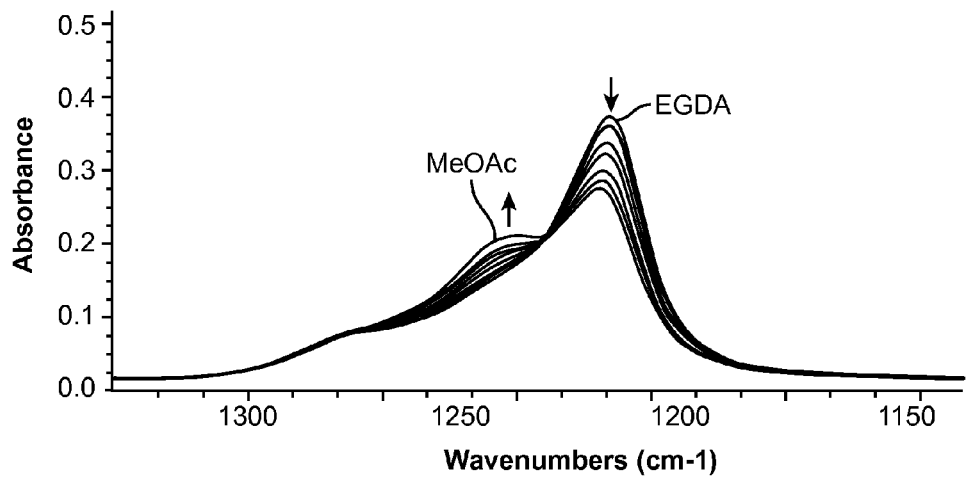
FIG. 9 is a graphic illustration of the overlaid infrared spectra obtained during the course of a reaction of 2:1 Molar ratio MeOH:EGDA at 0.0 degrees Celsius over a time span of 6.5 hours.

As can be seen in FIG. 9, the reaction takes place at a much slower rate and the formation of MeOAc is substantially inhibited at the lower reaction temperature 0 degrees Celsius. Moreover, the EGDA remains largely present after a 6.5 hour run of the experiment.

Example 3

Figure 10:
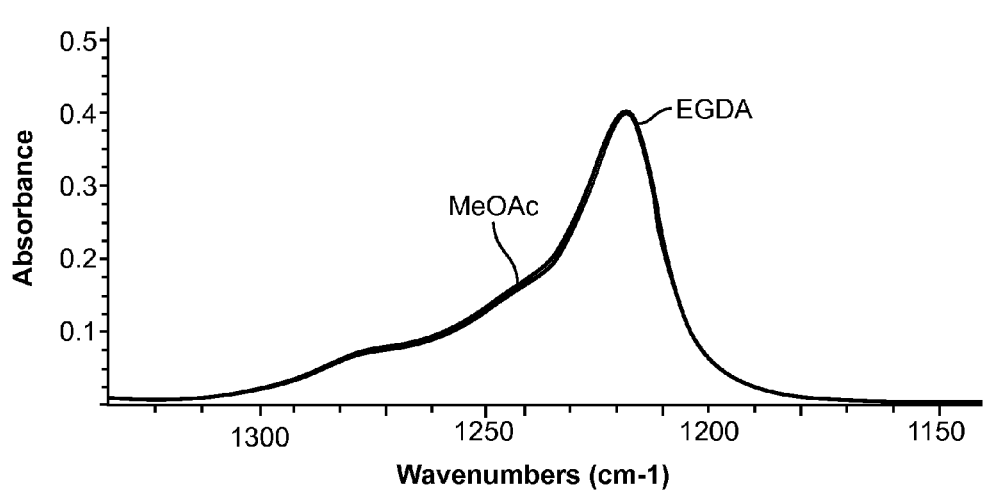
FIG. 10 is a graphic illustration of the overlaid infrared spectra obtained during the course of a reaction of 2:1 Molar ratio MeOH:EGDA at 22.5 degrees Celsius over a time span of 6.5 hours with no catalyst present.

The reaction of Example 1 was also carried out without the aid of a catalyst. As can be seen, by inspection of FIG. 10, there is no MeOAc peak, thereby indicating that no reaction has taken place in the absence of the acid catalyst.

Example 4

The reaction of Example 1 was carried out at 49 degrees Celsius with multiple concentrations of PTSA catalyst. Specifically, there are four separate experiments, the data from those experiments are presented in FIG. 6. Specifically, the four runs are at 0.5 wt %, 1.5 wt %, 3 wt %, and 5 wt % PTSA catalyst. As can be seen by inspection of FIG. 6, the rate increased with increasing catalyst concentration, with the 5 wt % PTSA catalyst having the fastest reaction rate while the reaction with 0.5 wt % PTSA is the slowest reaction rate. Therefore, FIG. 6 supports the above disclosure that PTSA catalyst concentration can be used to affect the rate of methanolysis.

Example 5

The reaction of Example 1 was carried out at 60 degrees Celsius with a 6:1 MeOH:EGDA molar ratio and 5 wt % PTSA catalyst. Data for this run are shown in FIG. 4.

Example 6

The reaction of Example 1 was carried out at 60 degrees Celsius with a 6:1 HOAc:EGDA ratio and 5 wt % PTSA catalyst. Data for this run are shown in FIG. 4. Overlaid infrared spectra associated with this run are shown in FIG. 2.

Example 7

The reaction of Example 1 was carried out at multiple temperatures with a 6:1 MeOH:EGDA ratio and 0.5 wt % PTSA catalyst. Specifically, the temperatures were measured at 19 degrees Celsius, 34 degrees Celsius, and 49 degrees Celsius. The results of these experiments are presented in Table 2.

The various embodiments, figures, and examples described above are provided by way of illustration only and should not be construed to limit the disclosure. Those skilled in the art will readily recognize various modifications and changes that may be made to the present disclosure without following the example embodiments and applications illustrated and described herein, and without departing from the true spirit and scope of the present disclosure.

We claim:

1. A process for the production of vinyl acetate comprising:
   reacting ethylene, acetic acid, and oxygen in the presence of a catalyst to produce a reaction mixture comprising vinyl acetate and ethylene glycol diacetate;
   separating the reaction mixture to form a gas stream and a crude vinyl acetate stream comprising vinyl acetate, and ethylene glycol diacetate;
   separating the ethylene glycol diacetate from said crude vinyl acetate stream; and
   methanolyzing the separated ethylene glycol diacetate in the presence of a methanolyzing catalyst and recovering methyl acetate.

2. The process of claim 1 wherein the ethylene glycol diacetate stream comprises at least 50 wt % ethylene glycol diacetate.

3. The process of claim 1 wherein the methanolyzing of the ethylene glycol diacetate reaches an equilibrium of greater than about 95% completion.

4. The process of claim 1 wherein the methanolyzing of the ethylene glycol diacetate reaches an equilibrium of about 100% completion.

5. The process of claim 1 wherein the methanolyzing step further comprises methanolyzing the ethylene glycol diacetate stream in a boiling pot reactor.

6. The process of claim 5, wherein the boiling pot reactor operates within the temperature range from about 60 degrees Celsius to about 80 degrees Celsius.

7. The process of claim 1 further comprising the step of recycling the methyl acetate to an acetic acid reactor.

8. The process of claim 1, the reaction mixture further comprising carbon dioxide, acetic acid, water, and ethyl acetate.

9. The process of claim 1 the gas stream further comprising ethylene and carbon dioxide.

10. The process of claim 1 the crude vinyl acetate stream further comprising acetic acid, water, and ethyl acetate.

11. The process of claim 1 wherein the methyl acetate is recovered in a distillation tower.

* * * * *